United States Patent [19]
Levina et al.

[11] Patent Number: 5,955,590
[45] Date of Patent: Sep. 21, 1999

[54] CONJUGATES OF MINOR GROOVE DNA BINDERS WITH ANTISENSE OLIGONUCLEOTIDES

[75] Inventors: Asya Levina; Paul C. Zamecnik, both of Shrewsbury, Mass.

[73] Assignee: Worcester Foundation for Biomedical Research, Shrewsbury, Mass.

[21] Appl. No.: 08/680,350

[22] Filed: Jul. 15, 1996

[51] Int. Cl.$^6$ .............................. C07H 21/00; C07H 21/04
[52] U.S. Cl. .......................................... 536/23.1; 536/24.5
[58] Field of Search ............................ 435/6, 7.1; 514/2, 514/18, 19, 44; 530/300, 331; 260/998.2; 536/23.1, 24.3, 24.5

[56] References Cited

U.S. PATENT DOCUMENTS

| | | | |
|---|---|---|---|
| 5,198,346 | 3/1993 | Ladner et al. | 435/69.1 |
| 5,258,507 | 11/1993 | Cruickshank et al. | 536/24.3 |
| 5,405,938 | 4/1995 | Summerton et al. | 528/406 |
| 5,437,977 | 8/1995 | Segev | 435/6 |
| 5,446,137 | 8/1995 | Maag et al. | 536/23.1 |
| 5,466,786 | 11/1995 | Buhr et al. | 536/26.26 |
| 5,493,012 | 2/1996 | Bokita et al. | 536/26.6 |
| 5,514,786 | 5/1996 | Cook et al. | 536/23.1 |
| 5,519,126 | 5/1996 | Hecht | 536/21.02 |
| 5,693,463 | 12/1997 | Edwards et al. | 435/6 |
| 5,716,780 | 2/1998 | Edwards et al. | 435/6 |
| 5,738,990 | 4/1998 | Edwards et al. | 435/6 |
| 5,744,131 | 4/1998 | Edwards et al. | 424/78.08 |
| 5,786,138 | 7/1998 | Swenson | 435/6 |

FOREIGN PATENT DOCUMENTS

| | | |
|---|---|---|
| WO92/20698 | 11/1992 | WIPO . |
| WO/93/03736 | 3/1993 | WIPO . |
| WO/94/17092 | 8/1994 | WIPO . |
| PCT/US97/ 12311 | 10/1997 | WIPO . |

OTHER PUBLICATIONS

Lown, JW., "DNA Recognition by Lexitropsins, Minor Groove Binding Agents", *J Mol. Rec.*, (1994), 7:79–88.

Lukhtanov, EA., et al., "Oligodeoxyribonucleotides with Conjugated Dihydropyrroloindole Oligopeptides: . . . Properties", *Bioconjugate Chem*, (1995), 6:418–426.

Levina, A., et al., "Conjugates of Minor Groove DNA Binders with Oligodeoxynucleotides: Synthesis and Properties", *Antisense & Nucleic Drug Development*, (1996), 6:75–85.

Waring, M., et al., "Binding of Antibiotics to DNA", *Host–Guest Molecular Interactions: From Chemistry to Biology* / Wiley, Chichester (Ciba Foundation Symposium 158), 1991, pp. 128–146.

Lown, William, J., "DNA Recognition by Lexitropsins, Minor Groove Binding Agents", *Journal of Molecular Recognition*, 1994, 7:79–88.

Pilch, D., et al., "Ligand–induced formation of nucleic acid triple helices", *Proc. Natl. Acad. Sci.*, 1994, 91:9332–9336.

Wittung, P., et al., "Interactions of DNA binding ligands with PNA–DNA hybrids", *Nucleic Acids Research*, 1994, 22:24:5371–5377.

Sinyakov, A., et al., "Exceptional and Selective Stabilization of A–T Rich DNA–DNA Duplexes by N–Methylpyrrole Carboxamide Peptides Conjugated to Oligodeoxynucleotides". *Journal of the American Chemical Society*, 1995, 117: 4995–4996.

*Primary Examiner*—George C. Elliott
*Assistant Examiner*—Thomas G. Larson
*Attorney, Agent, or Firm*—Wolf, Greenfield & Sacks, P.C.

[57] ABSTRACT

Compositions of antisense oligonucleotides conjugated to peptides of a plurality of N-methylpyrrolecarboxamides linked by peptide bonds is provided. The compositions form stable hybridization complexes with DNA and can be used for any purpose which involves hybridizing an oligonucleotide to a DNA molecule, such as in antisense procedures. A method for enhancing oligonucleotide binding to a target is also provided. The method involves the step of hybridizing the target DNA with an oligonucleotide-peptide composition.

24 Claims, No Drawings

CONJUGATES OF MINOR GROOVE DNA BINDERS WITH ANTISENSE OLIGONUCLEOTIDES

GOVERNMENT FUNDING

This work was funded in part by the National Institutes of Health under Grant No. 2U O1.A1-24846-09. The government may have certain rights to this invention.

FIELD OF THE INVENTION

This invention relates to novel compositions of antisense oligonucleotides coupled to an N-methylpyrrolecarboxamide.

BACKGROUND OF THE INVENTION

Over the past few years it has been observed that several types of molecules can bind to DNA and disrupt the function of DNA. Some of these molecules are presently used as antimicrobials and others are used as cancer chemotherapeutics. In the former case, the microbe is inhibited from replicating, and in the latter case, the cancer cell is inhibited from replicating.

DNA-binding molecules may be categorized based on the type of interaction that occurs between the DNA and the DNA-binding molecule. These types of interactions include electrostatic interactions, covalent binding, intercalation, and reversible groove-binding (most commonly in the minor groove of the B-form DNA helix). Certain DNA-binding molecules involve more than one of these interactions, such as diamidino-2-phenylindole (DAPI), which is able to both intercalate and bind within the grooves of DNA.

Of the four categories of DNA-binding molecules the intercalators and the groove binders are the most common. Intercalators function by causing a local fixation withouut unwinding and extension of the DNA helix, with the intercalator positioning itself between the base pairs. Common antibiotics which are intercalators are anthracyclines, nogalamycin, and actinomycin. The groove binders function by binding in the grooves of the helix. The most common groove binders are the N-methylpyrrole peptides, such as netropsin and distamycin.

The distortion caused by groove binding is significantly less than that associated with intercalators. As a result, intercalating agents have attracted more attention than groove binders as therapeutic agents.

The stabilization of short duplexes by intercalating agents has been recognized for many years. This phenomenon of stabilization has been applied to the antisense field. A duplex formed by an antisense molecule and its DNA or RNA target is significantly stabilized by free intercalating agents, thereby enhancing the effectiveness of the antisense molecule. Such intercalating agents have been found to stabilize such duplexes even when covalently bound to the antisense molecule.

As with intercalation agents, it has been observed that free distamycin and netropsin when added to a DNA duplex will stabilize that duplex. (They will not, however, stabilize a DNA-RNA duplex.) These molecules are believed to displace the natural hydration from AT-rich regions of the minor groove of the duplex. At this AT-rich region of the DNA duplex, the free distamycin or netropsin form bifurcated hydrogen bonds with adenine N-3 and thymine O-2 atoms and numerous van der Waals contacts with various atoms in the nucleotide backbone. These atomic interactions stabilize the DNA-distamycin or netropsin structure and, in turn, effectively strengthen the interaction of the two DNA strands.

In order to interfere with the replication or transcription of a specific DNA molecule researchers have used a combination of free netropsin or distamycin and antisense oligonucleotides having AT rich regions. The antisense oligonucleotide binds to the specific DNA sequence and the free netropsin or distamycin interacts with the minor groove and strengthens the DNA antisense oligonucleotide complex, thereby making the antisense molecule more effective at inhibiting the formation of a transcription bubble and inhibiting transcription.

It recently was attempted to covalently attach N-methylpyrrolecarboxamides (MPCs) to short oligodeoxynucleotides to determine whether the tethered MPCs could still function to stabilize a DNA-DNA duplex. Sinyakov, A. N., et al., *J Am. Chem. Soc.*, 117:4995–4996, (1995). The short oligodeoxynucleotides used were either poly A or poly T, and the target DNA likewise was poly A or poly T sequences. Neither netropsin nor distamycin were attached to these oligodeoxynucleotides. Instead, synthetic MPCs were used, having 2, 3, 4, or 5 methylpyrrolecarboxamide moieties. The MPC was attached to the oligodeoxynucleotide by the carbon atom at the 3C position of the pyrrole moiety of the N-terminal N-methylpyrrolecarboxamide. The following structure is an example of the complexes disclosed in Sinyakov et al.:

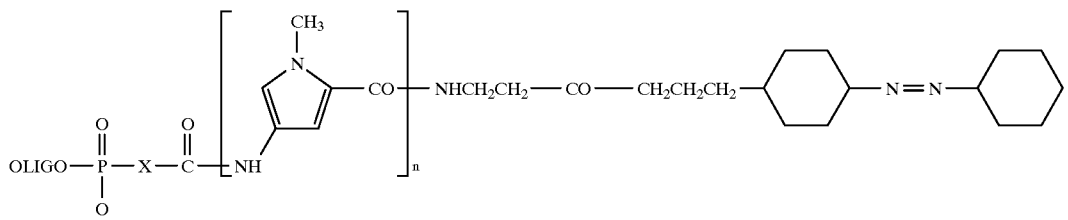

wherein n=2–5 and wherein X is a linker.

The MPC-oligodeoxynucleotide complex was hybridized with DNA and the resultant MPC-oligodeoxynucleotide/DNA duplex was subjected to melting conditions to determine the melting temperature of the complex. The melting temperature was compared to the melting temperature of the DNA duplex in the absence of N-methylpyrrolecarboxamide and to the melting temperature of the DNA duplex in the presence of a free N-methylpyrrolecarboxamide, in particular, free distamycin.

A number of observations emerged from the results of this study. Firstly, the tethered MPCs stabilized the duplexes as in all instances versus the duplex in the absence of any free distamycin. Secondly, the degree of stabilization was a function of MPC peptide length, with an MPC having two N-methylpyrrolecarboxamide moieties showing the least stabilization and an MPC having 5

N-methylpyrrolecarboxamide moieties showing the most stabilization. The difference between MPCs with 2 and 3 N-methylpyrrolecarboxamide moieties was most pronounced with 3 such moieties increasing the melting temperature by about nine degrees more than the melting temperature with two such moieties. Thirdly, when the MPCs were tethered to poly A deoxynucleotides, only the covalent complex using an MPC having 5 N-methylpyrrolecarboxamide moieties had a better stabilization effect than free distamycin. When the MPCs were tethered to poly T deoxynucleotides, only the covalent complexes using an MPC having 4 and 5 N-methylpyrrolecarboxamide moieties had a substantially better stabilization effect versus free distamycin ($\Delta T_m$=13 and 18 respectively), whereas the MPC with 2 such moieties did not work as well as free distamycin and the MPC with 3 such moieties worked about the same as free distamycin ($\Delta T_m \approx 5$). Finally, the MPC peptide was found to be more effective at stabilizing the complex when it was covalently attached to poly(dT)$_8$ than to poly(dA)$_8$.

SUMMARY OF THE INVENTION

The present invention involves the unexpected finding that N-methylpyrrolecarboxamides attached to oligodeoxynucleotides via the 1C position of the C terminal pyrrole moiety have improved properties. It further involves the unexpected finding that netropsin tethered to oligodeoxynucleotides are substantially superior at stabilizing DNA duplexes than free netropsin. It further involves the unexpected finding that two distamycin molecules attached to a single oligodeoxynucleotide are substantially superior at stabilizing DNA duplexes than free distamycin. It also involves the discovery that linkers of a variety of lengths can influence DNA duplex/MPC stabilization and that oligonucleotide-MPC conjugates can stabilize adjacent oligonucleotide DNA duplexes.

The oligonucleotide-peptide conjugates of the invention are useful in situations when it is desirable to form stable complexes of a single strand of a DNA molecule complexed with a complementary oligonucleotide, such as in antisense DNA procedures and in DNA detection systems using a labeled oligonucleotide probe. The oligonucleotide-peptide conjugates of the invention may be hybridized with a DNA molecule to form a double stranded nucleic acid sequence composed of a DNA-oligonucleotide/peptide complex. The peptide conjugated to the oligonucleotide stabilizes the DNA-oligonucleotide interaction. The resultant DNA-oligonucleotide duplex is more stable and has a higher melting temperature than the same DNA-oligonucleotide duplex that does not have a peptide conjugated to the oligonucleotide or even one which has a peptide added as a free group. The stable DNA-oligonucleotide complex does not disassociate under physiological conditions as readily as a nonstabilized duplex, and, therefore, the oligonucleotide does not separate as readily from the DNA to permit formation of a transcription bubble. The enhanced stability of the composition of the invention in this manner reduces the ability of the DNA strand to undergo transcription. The composition of the invention likewise allows a stronger reaction to be produced between DNA and the oligonucleotide, when the oligonucleotide is used as a probe, such that the oligonucleotide functions as a more efficient probe than an oligonucleotide not conjugated to a peptide.

In one embodiment the composition is a single antisense oligonucleotide having at least four consecutive nucleic acids selected from the group consisting of A and T and conjugated to a peptide. The oligonucleotide hybridizes to a target DNA and the peptide conjugated to the oligonucleotide interacts with the double stranded target DNA-oligonucleotide complex in the region of the at least four consecutive A and/or T residues. The binding of the peptide stabilizes the double stranded target nucleic DNA complex.

In another embodiment the composition is a first oligonucleotide which is conjugated to a peptide but which does not have at least four consecutive nucleic acids selected from the group consisting of A and T. The peptide conjugated to the first oligonucleotide is able to stabilize the interaction between a second oligonucleotide and the target DNA when both the first and second oligonucleotides are hybridized adjacent to one another on the target DNA.

According to one aspect of the invention, an antisense oligonucleotide is covalently coupled to a peptide composed of a plurality of N-methylpyrrolecarboxamides linked by peptide bonds. The C-terminal N-methylpyrrolecarboxamide has a pyrrole moiety with a carbon atom at the 1C position, adjacent a nitrogen atom of the pyrrole moiety, to which the antisense oligonucleotide is covalently coupled. Preferably the peptide includes between two and five N-methylpyrrolecarboxamides. The antisense oligonucleotide has at least four consecutive nucleic acids selected from the group consisting of A and T. In one embodiment the consecutive nucleic acids are selected from the group consisting of TTAAA, TTTAA, AATT, TTAAT, AATTA, TAATA, ATTAT, AAAA, TTTT, ATAT, and TATA. In one embodiment the oligonucleotide is coupled to a single peptide consisting of netropsin. In another embodiment the oligonucleotide is coupled to two peptides, each consisting of distamycin.

According to another aspect of the invention, there is provided an antisense oligonucleotide covalently coupled to netropsin. The antisense oligonucleotide, in one embodiment, may be coupled to only a single netropsin. The antisense oligonucleotide is coupled to netropsin via a linker which is tethered to netropsin by the terminal amidine functionality of the netropsin. In one embodiment the composition consists essentially of

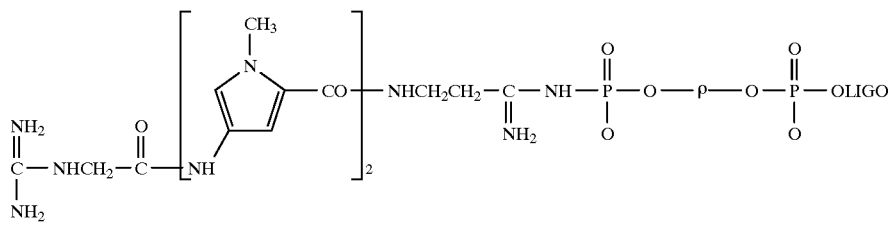

wherein ρ is an organic linker comprising a chain length between 1and 30 a toms or is a bond. Preferably, the composition includes an antisense oligonucleotide having at least four consecutive amino acids selected from the group consisting of A and T. In one embodiment the consecutive nucleic acids are selected from the group consisting of TTAAA, TTTAA, AATT, TTAAT, AATTA, TAATA, ATTAT, AAAA, TTTT, ATAT, and TATA.

According to another aspect of the invention, there is provided an antisense oligonucleotide with a 5' end and a 3' end. The antisense oligonucleotide is covalently coupled to two distamycin's, one distamycin covalently coupled to the 5' end and the other distamycin covalently coupled to the 3' end of the antisense oligonucleotide. In one embodiment the antisense oligonucleotide is coupled to each distamycin via a linker which is tethered to each distamycin by a terminal amidine functionality of the distamycin. In one embodiment, the composition consists essentially of the target DNA adjacent to the first portion. The first antisense oligonucleotide is covalently linked to a peptide having a plurality of N-methylpyrrolecarboxamides linked to one another by peptide bonds. The first oligonucleotide is free of regions having at least four consecutive nucleic acids selected from the group consisting of A and T. The second antisense oligonucleotide has at least four consecutive nucleic acids selected from the group consisting of A and T. In one embodiment the second antisense oligonucleotide comprises consecutive nucleic acids selected from the group consisting of TTAAA, TTTAA, AATT, TTAAT, AATTA, TAATA, ATTAT, AAAA, TTTT, ATAT, and TATA.

In one aspect of the invention each of the compositions described above is formulated as a pharmaceutical composition having an effective amount of the composition and a pharmaceutically acceptable carrier described above.

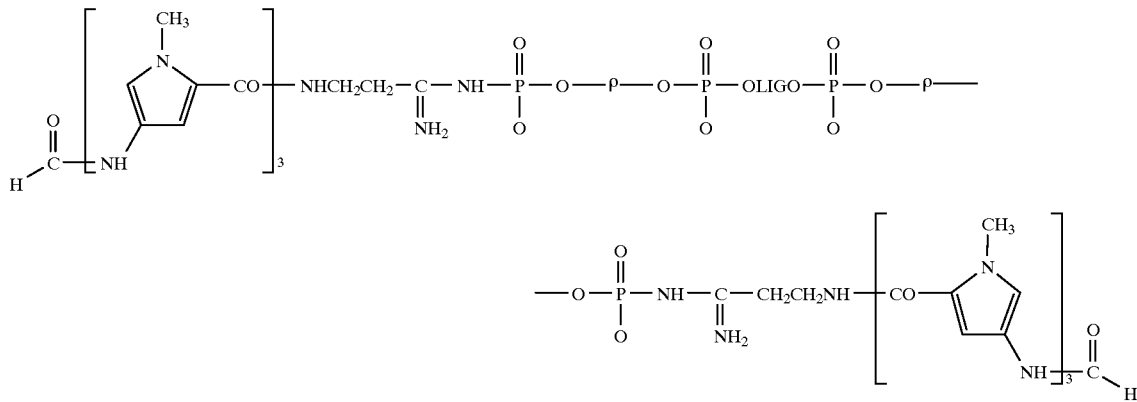

wherein ρ is an organic linker comprising a chain length between 1 and 30 atoms or is a bond. Preferably, the composition includes an antisense oligonucleotide having at least four consecutive amino acids selected from the group consisting of A and T. In one embodiment the consecutive nucleic acids are selected from the group consisting of TTAAA, TTTAA, AATT, TTAAT, AATTA, TAATA, ATTAT, AAAA, TTTT, ATAT, and TATA.

Another composition of matter including an antisense oligonucleotide covalently coupled to a peptide is also provided. In this aspect of the invention the peptide has a plurality of N-methylpyrrolecarboxamides linked to one another by peptide bonds and wherein the antisense oligonucleotide is free of segments comprising at least four consecutive nucleic acids selected from the group consisting of A and T and, more particularly, is free of segments comprising consecutive nucleic acids selected from the group consisting of TTAAA, TTTAA, AATT, TTAAT, AATTA, TAATA, ATTAT, AAAA, TTTT, ATAT, and TATA. The composition of matter may be used in combination with a second antisense oligonucleotide having at least four consecutive nucleic acids selected from the group consisting of A and T. The first and second antisense oligonucleotides hybridize adjacent to one another on a target DNA, and the peptide on the first oligonucleotide stabilizes the AT rich region on the duplex created by the second oligonucleotide hybridized to the target DNA.

According to yet another aspect of the invention a kit for enhancing binding of an oligonucleotide to a target DNA is provided. The kit includes a first antisense oligonucleotide that binds to a first portion of the target DNA and a second antisense oligonucleotide that binds to a second portion of According to another aspect of the invention a method for enhancing binding of an antisense oligonucleotide to a target DNA is provided. The method includes the step of contacting the target DNA with one of the compositions of the invention descibed above.

DETAILED DESCRIPTION OF THE INVENTION

The compositions of the invention are improved oligonucleotide-peptide conjugates that are useful for a variety of functions, such as for therapeutic antisense procedures and DNA probes. The improved oligonucleotide-peptide conjugates include an antisense oligonucleotide conjugated to a peptide comprising a plurality of N-methylpyrrolecarboxarnide moieties. In some embodiments the peptide is a single peptide chain of two N-methylpyrrolecarboxamide moieties which is netropsin and in other embodiments the peptide is two peptide chains each having three N-methylpyrrolecarboxamide moieties, which is distamycin. In one aspect of the invention the oligonucleotide-peptide conjugate has an A-T rich region. According to another aspect, however, the oligonucleotide-peptide conjugate does not have an A-T rich region but is used in combination with an oligonucleotide that has an A-T rich region.

The peptide can be tethered to the oligonucleotide by an organic linker, such that the antisense oligonucleotide is linked to the carboxyl group of the C-terminal end of the peptide. The oligonucleotide may be attached to the linker by either its 5' or 3' end. The linker and its relation to the oligonucleotide and the peptide is provided in more detail below. The following structure illustrates the general structure of the interaction between the oligonucleotide, the linker, and the peptide, which is a plurality of N-methylpyrrolecarboxamide moieties and other than a phosphate at the 5' position. In addition, modified oligonucleotides may include sugars such as arabinose instead of deoxyribose.

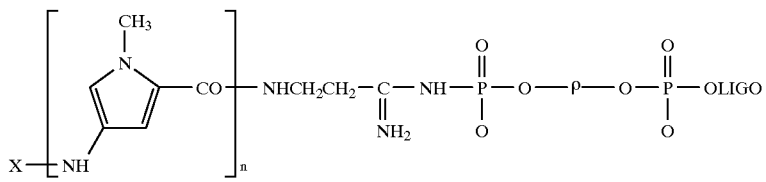

wherein X is a small non-reactive side group and wherein n represents the number of repeating N-methylpyrrolecarboxamide moieties. The value of n may be anywhere in the range of 1 to 10 but is more preferably 2 to 5. X may be, for example, either of the following structures:

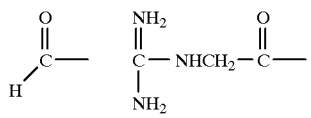

The invention involves the use of antisense oligonucleotides. As used herein, the term "antisense oligonucleotide" or "antisense" describes an oligonucleotide that is an oligodeoxyribonucleotide or a modified oligodeoxyribonucleotide which hybridizes under physiological conditions to a nucleic acid molecule comprising a particular gene and, thereby, inhibits the transcription of that gene. In one set of embodiments, the antisense oligonucleotides of the invention may be composed of "natural" deoxyribonucleotides. That is, the 5' end of one native nucleotide and the 3' end of another native nucleotide may be covalently linked, as in natural systems, via a phosphodiester internucleoside linkage. These oligonucleotides may be prepared by art recognized methods which may be carried out manually or by an automated synthesizer.

In preferred embodiments, however, the antisense oligonucleotides of the invention also may include "modified" oligonucleotides. That is, the oligonucleotides may be modified in a number of ways which do not prevent them from hybridizing to their target but which enhance their stability or targeting or which otherwise enhance their therapeutic effectiveness.

The term "modified oligonucleotide" as used herein describes an oligonucleotide in which (1) at least two of its nucleotides are covalently linked via a synthetic internucleoside linkage (i.e., a linkage other than a phosphodiester linkage between the 5' end of one nucleotide and the 3' end of another nucleotide) and/or (2) a chemical group not normally associated with nucleic acids has been covalently attached to the oligonucleotide. Preferred synthetic internucleoside linkages are phosphorothioates, alkylphosphonates, phosphorothioates, phosphate esters, alkylphosphonothioates, phosphoramidates, carbamates, carbonates, phosphate triesters, acetamidates, and carboxymethyl esters.

The term "modified oligonucleotide" also encompasses oligonucleotides with a covalently modified base and/or sugar. For example, modified oligonucleotides include oligonucleotides having backbone sugars which are covalently attached to low molecular weight organic groups other than hydrogen at the 2' position, hydroxyl group at the 3' position The antisense molecules are designed so as to interfere with transcription of a target gene upon hybridization with the target gene. Those skilled in the art will recognize that the exact length of the antisense oligonucleotide and its degree of complementarily with its target will depend upon the specific target selected, including the sequence of the target and the particular bases which comprise that sequence. It is preferred that the antisense oligonucleotide be constructed and arranged so as to bind selectively with the target under physiological conditions, i.e., to hybridize substantially more to the target sequence than to any other sequence in the target cell under physiological conditions.

In order to be sufficiently selective and potent for inhibition, such antisense oligonucleotides should comprise at least 5 and, more preferably, at least 10 consecutive bases which are complementary to the target. Most preferably, the antisense oligonucleotides comprise a complementary sequence of 10–20 bases. Oligonucleotides that are attached to a peptide are more stable than oligonucleotides that are not attached to a peptide. Therefore, it is possible to use oligonucleotides having shorter lengths for antisense procedures when using oligonucleotides conjugated to a peptide than one would traditionally use for unattached antisense oligonucleotides. Although oligonucleotides may be chosen which are antisense to any region of the gene, in preferred embodiments the antisense oligonucleotides correspond to N-terminal or 5' upstream sites such as, transcription initiation or promoter sites.

The use of the peptide conjugated to an antisense oligonucleotide molecule is desirable in virtually any medical condition wherein a reduction in the expression of the target gene is desirable. The target gene that is used will depend on which physiological result is desired. Since virtually all genes have at least four consecutive nucleotides selected from the group consisting of A and T, a target gene may be selected based on the knowledge that a particular gene causes the physiological condition that it is desirable to eliminate. One of skill in the art can easily choose and synthesize any of a number of appropriate antisense molecules for use in accordance with the present invention, by screening any of the widely available sequence databases for a particular gene of interest. Regions within the sequence of the gene having at least four consecutive nucleic acids selected from the group consisting of A and T may be easily identified by one of ordinary skill in the art using conventional techniques such as a DNA sequencing reaction or by manual or computer scans of the sequence. A preferred target gene is the gag gene of HIV described in Temsamani et al., *Antisense Research and Development V*. 4, p. 279–284 (1994), which is hereby incorporated by reference.

The invention embraces a peptide which is composed of a plurality of N-methylpyrrolecarboxamide moieties coupled to an antisense oligonucleotide that has an A-T rich region. Alternatively the invention embraces an N-methylpyrrolecarboxamide coupled to an antisense oligonucleotide that does not have an A-T rich region, but that is used in conjunction with an oligonucleotide having an A-T rich region. As used herein the term "A-T rich region" includes any nucleic acid molecule having at least four consecutive nucleotides selected from the group consisting of adenine (A) and thymidine (T). The A and/or T residues within the A-T rich region of the oligonucleotide may be, present in any combination or in any arrangement. For example, the arrangement of A and/or T residues within the A-T rich region may include but is not limited to any of the following sequences: TTAAA, TTTAA, AATT, TTAAT, AATTA, TAATA, ATTAT, AAAA, TTTT, ATAT, and TATA.

As mentioned above, the invention encompasses two different embodiments: (1) an A-T rich oligonucleotide-peptide conjugate and (2) a combination of an A-T 'poor' oligonucleotide-peptide conjugate and a nonconjugated A-T rich oligonucleotide. The two embodiments involve structurally different oligonucleotides but they are useful for the same purposes and function in a similar manner. In both cases, the antisense oligonucleotide binds to the target gene and the peptide interacts with an A-T rich region of an oligonucleotide-nucleic acid complex to stabilize the complex. The two embodiments differ, however, in that the single oligonucleotide-peptide conjugate includes an A-T rich region and functions by itself. Once the oligonucleotide has bound to the target gene, the peptide conjugated to that oligonucleotide interacts with the A-T rich region of the formed duplex to stabile the duplex. In the embodiment involving two oligonucleotides, the first oligonucleotide, which is bound to the peptide, binds to its complementary sequence in the target gene. This sequence does not include an A-T rich region. The second oligonucleotide, which is not covalently conjugated to a peptide but which includes an A-T rich region, also binds to a complementary sequence in the target gene adjacent to the first oligonucleotide-target duplex. Once both oligonucleotides are bound to the target gene, the peptide conjugated to the first oligonucleotide interacts with the A-T rich region in the duplex formed by the second oligonucleotide and the target gene to stabilize that duplex.

The compositions of the invention include oligonucleotides conjugated to a peptide, wherein the peptide is a plurality of N-methylpyrrolecarboxamide moieties. N-methylpyrrolecarboxamide moieties are well known in the art and have been described in many publications including Sinyakov et al., Supra and Grehn. L: Ragnarsson, U. J. Org. Chem. (1981) 46:3492. N-methylpyrrolecarboxamide's have the following general structure:

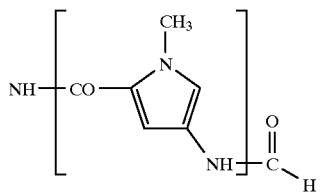

In one embodiment of the invention an antisense oligonucleotide is covalently coupled to netropsin. Netropsin has the following structure:

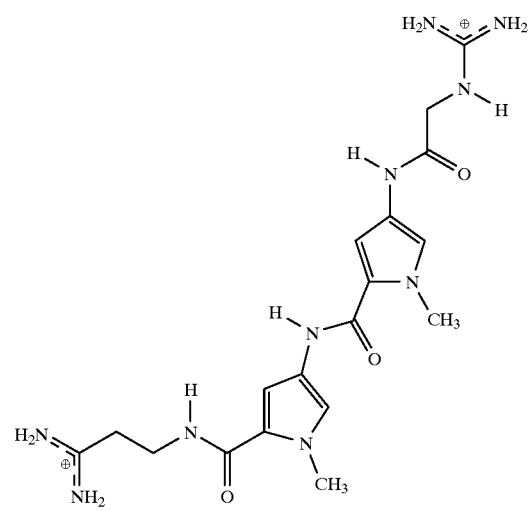

The Sinyakov reference, (Sinyakov, supra) discloses the use of a composition having two N-methylpyrrolecarboxamide moieties. It was observed, however, that this composition did not stabilize the oligonucleotide-DNA complex as well as a composition having three N-methylpyrrolecarboxamide moieties, suggesting that three N-methylpyrrolecarboxamide moieties was more effective at stabilizing an oligonucleotide-target gene complex than two moieties. In contrast to the teaching of the prior art reference, it was surprisingly found that a single covalently attached netropsin which has only two N-methylpyrrolecarboxamide moieties was more effective at stabilizing the oligonucleotide-gene complex than a single covalently attached distamycin, which has three such moieties. It also was discovered, surprisingly in contrast to the prior art, that covalently attached netropsin was much more effective at stabilizing a duplex than was free netropsin.

According to this embodiment of the invention, netropsin is coupled to the oligonucleotide through a linker as described briefly above. The netropsin is tethered to the oligonucleotide by an organic linker, which joins the C-terminal pyrrole moiety of the netropsin to the antisense oligonucleotide. In general, the peptide is connected to the oligonucleotide via the carboxyl group at the C-terminal end of the peptide. The carboxyl group is attached to the carbon at the 1C position adjacent the nitrogen of the pyrrole moiety of the C-terminal N-methylpyrrolecarboxamide. More specifically, in this embodiment the oligonucleotide is attached via a linker to netropsin's terminal amidine group extending from the C-terminal carboxyl group at the 1C position of the pyrrole moiety of the C-terminal N-methylpyrrolecarboxamide. The oligonucleotide may be attached to the linker by either its 5' or 3' end. The following structure illustrates the atomic interactions involved in the bond between the oligonucleotide and the netropsin:

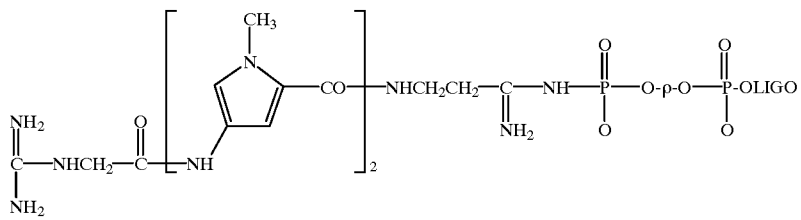

wherein ρ is an organic linker typically of a chain length between 1 and 30 atoms or is a bond.

Although a recent paper by Sinyakov et al., supra disclosed oligonucleotides conjugated to N-methylpyrrolecarboxamides the Sinyakov compositions are considerably different from the compositions of the present invention. The Sinyakov compositions have an oligonucleotide linked to the 3C position of the pyrrole moiety of the N-terminal N-methylpyrrolecarboxamide, whereas the oligonucleotide-peptide conjugates of the present invention have an oligonucleotide linked to the C-terminal N-methylpyrrolecarboxamide at the 1C position adjacent the nitrogen atom of the pyrrole moiety.

An "organic linker" as used herein includes a chemical bond and/or an atom or chain of atoms. It may be virtually any practical length to enhance binding stability of the oligonucleotide-peptide conjugate, although backbone chain lengths of between 3 and 18 atoms have been found to be useful. It preferably is 18 backbone atoms in length, which appears to provide a desirable length to permit the enhanced stability of the conjugate. Longer chains are possible, although unnecessary and impractical to make due to the extra length and depending upon the components of the chain and any side groups. The length of the linker, however, also may be chosen to optimize binding when the A-T rich region is in a second oligonucleotide which is proximal to the oligonucleotide conjugated to the peptide.

The organic linker should be physiologically compatible when used in vivo. It thus may be composed of any atoms found within a physiological environment or found to be biologically nontoxic when in the form of the linker. Although C, H, O, S, N, and P have been found to be useful, the linker is not limited to these atoms. The atoms may be present in varying amounts and combinations. For example, a linker may be composed of primarily C atoms but may include other atoms such as O or H which can chemically interact with C. When the composition is used in vitro, the linker does not have to be physiologically compatible. The linker may also be a straight backbone chain of atoms or may include branches of atoms extending off the backbone chain. The linker may be saturated or unsaturated. Linkers useful in the compositions of the invention, for example, include the following molecules:

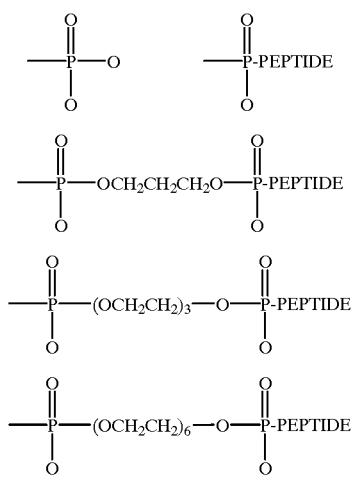

According to another aspect of the invention a composition of matter having an antisense oligonucleotide with a 5' end and a 3' end. The antisense oligonucleotide is covalently coupled to two distamycin molecules, one distamycin covalently coupled to the 5' end and the other distamycin covalently coupled to the 3' end of the antisense oligonucleotide. The antisense oligonucleotide can be coupled to the distamycin molecules via linkers as described above. Each linker can be tethered to the distamycin via the distamycin terminal amidine group. This group extends from the C-terminal carboxyl group which is attached at the 1C position of the pyrrole moiety of the C-terminal N-methylpyrrolecarboxamide of the distamycin. The structure of the distamycin conjugated to oligonucleotide is shown below:

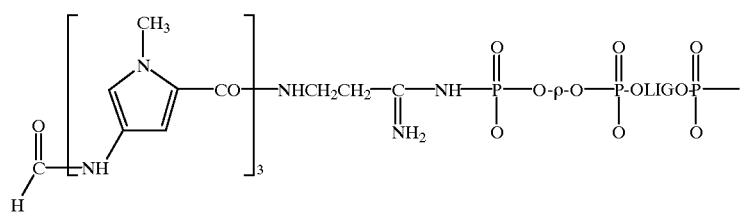

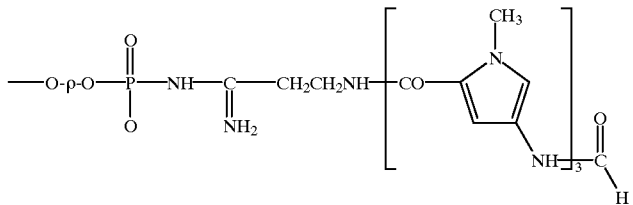

wherein ρ can be organic linker comprising a chain length between 1 and 30 atoms or is a bond.

Free distamycin has the following structure:

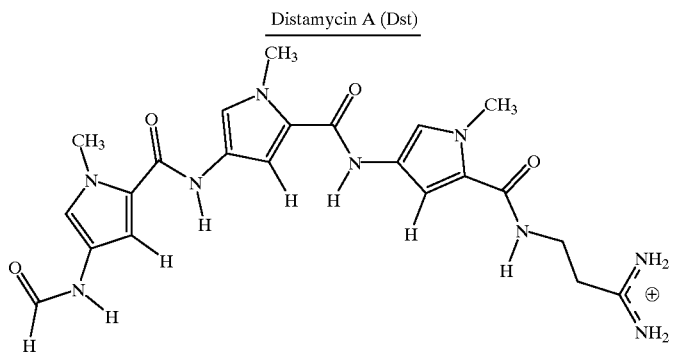

Distamycin A (Dst)

Prior to the present invention, distamycin molecules have not been conjugated to an oligonucleotide complex. Although peptide compositions having three N-methylpyrrolecarboxamide moieties have been conjugated to an oligonucleotide, distamycin has not previously been conjugated to an oligonucleotide. It was discovered, surprisingly, that a single distamycin molecule covalently attached to an oligonucleotide did not improve duplex stability at all, whereas two distamycin molecules covalently attached to an oligonucleotide not only improved duplex stability, but also substantially improved duplex stability versus the stability of the duplex in the presence of fee distamycin.

According to yet another aspect of the invention a kit for enhancing binding of an oligonucleotide to a target nucleic acid is provided. The kit includes a first antisense oligonucleotide that binds to a first portion of the target nucleic acid and a second antisense oligonucleotide that binds to a second portion of the target nucleic acid adjacent to the first portion. The first antisense oligonucleotide has at least four consecutive nucleic acids selected from the group consisting of A and T. The second antisense oligonucleotide is covalently linked to a peptide having a plurality of N-methylpyrrolecarboxamides linked to one another by peptide bonds. The second oligonucleotide preferably is free of A-T rich regions. In one embodiment the first antisense oligonucleotide comprises consecutive nucleic acids selected from the group consisting of TTAAA, TTTAA, AATT, TTAAT, AATTA, TAATA, ATTAT, AAAA, TTTT, ATAT, and TATA.

The oligonucleotide-peptide conjugate compositions of the invention may be used any time it is desirable to produce a DNA-oligonucleotide complex exhibiting enhanced stabilization properties. For example, it is desirable to produce a DNA-oligonucleotide complex exhibiting enhanced stabilization properties in antisense procedures, such as the use of antisense oligonucleotides to inhibit the catalytic function of enzymes involved in replication, transcription, or translation and in DNA selection procedures using an oligonucleotide probe.

The oligonucleotide-peptic conjugate is used as an antisense therapeutic agent by selecting an oligonucleotide that hybridizes under physiological conditions to a target nucleic acid. The oligonucleotide is one which hybridizes under physiological conditions to a region of a target nucleic acid which includes an A-T rich region or hybridizes under physiological conditions to a region of a target nucleic acid which is in close proximity to an A-T rich region. The peptide portion of the oligonucleotide interacts with the A-T rich region of the double stranded target nucleic acid sequence or the A-T rich region which is proximal to the double stranded target nucleic acid sequence. The peptide stabilizes the bonds of an A-T rich duplex and thus prevents the local region of DNA surrounding the A-T rich region from unwinding to form a transcription bubble. Because this region of DNA is unable to form a transcription bubble, transcription from the gene is inhibited and the protein encoded by the DNA is not produced.

The oligonucleotide-peptide conjugate is used also as an oligonucleotide probe when it is appropriate to identify a single nucleic acid sequence from a mixture of nucleic acid sequences and/or other components. An oligonucleotide that is complementary to the nucleic acid sequence and has an A-T rich region, or that hybridizes under physiological conditions to a region of a target nucleic acid which is in close proximity to an A-T rich region, is selected and conjugated to the peptide to produce the composition of the invention. The oligonucleotide may optionally be labeled with a detection reagent such as a dye, a fluorescent label or a radioactive label. The oligonucleotide-peptide is hybridized to the target nucleic acid sequence and the target nucleic acid is detected. In addition, or alternatively, the complex can be separated from the other target nucleic acid sequences and/or other components by any conventional technique, such as gel electrophoresis. Techniques for separating nucleic acid duplexes from nonduplexes are well known in the art.

The N-methylpyrrolecarboxamide coupled to an antisense oligonucleotide may be administered as part of a pharmaceutical composition. Such a pharmaceutical composition may include the N-methylpyrrolecarboxamide coupled to the antisense oligonucleotide in combination with any standard physiologically and/or pharmaceutically acceptable carriers which are known in the art. The compositions should be sterile and contain a therapeutically effective amount of the N-methylpyrrolecarboxamide coupled to the antisense oligonucleotide in a unit of weight or volume suitable for administration to a patient. The term "pharmaceutically acceptable" means a non-toxic material that does not interfere with the effectiveness of the biological activity of the active ingredients. The term "physiologically acceptable" refers to a non-toxic material that is compatible with a biological system such as a cell, cell culture, tissue, or organism. The characteristics of the carrier will depend on the route of administration. Physiologically and pharmaceutically acceptable carriers include diluents, fillers, salts, buffers, stabilizers, solubilizers, and other materials which are well known in the art.

When used therapeutically, the compounds of the invention are administered in therapeutically effective amounts. In general, a therapeutically effective amount means that amount necessary to delay the onset of, inhibit the progression of, or halt altogether the particular condition being treated. Generally, a therapeutically effective amount will vary with the subject's age, condition, and sex, as well as the nature and extent of the disease in the subject, all of which can be determined by one of ordinary skill in the art. The dosage may be adjusted by the individual physician or veterinarian, particularly in the event of any complication. A therapeutically effective amount typically varies from 0.01 mg/kg to about 1000 mg/kg, preferably from about 0.1 mg/kg to about 200 mg/kg and most preferably from about 0.2 mg//kg to about 20 mg/kg, in one or more dose administrations daily, for one or more days.

The therapeutics of the invention can be administered by any conventional route, including injection or by gradual infusion over time. The administration may, for example, be oral, intravenous, intraperitoneal, intramuscular, intracavity, subcutaneous, or transdermal. When using the antisense preparations of the invention, slow intravenous administration is preferred.

Preparations for parenteral administration include sterile aqueous or non-aqueous solutions. suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants chelating agents, and inert gases and the like.

The following non-limiting Examples provide further details of the invention.

EXAMPLES

Example 1

Preparation of Antisense Oligonucleotides Conjugated to Netropsin or Distamycin.

Methods:

In each of the following examples Netropsin and Distamycin were obtained from Boehringer Mannheim and Sigma, respectively. The melting transitions were measured at 260 or 320 nm using a Lambda 2 UV/VIS spectrometer (Perkin Elmer) fitted with a thermostat-controlled cell block. The temperature was increased at a rate of 1° C./minutes. Unless otherwise indicated, all reagents were obtained from Aldrich.

1. Analysis of compositions by Matrix-assisted laser desorption ionization-time of flight mass spectrometry (MALDI-TOFMS).

A matrix solution was made by dissolving 3-hydroxypicolinic acid (HPA) and N-(3-indolyl)-1-leucine (IAL) in 1:1 water/acetonitrile mixture. Concentrations of HPA and IAL were 70 g/L and 16 g/L, respectively. To reduce the formation of sodium and potassium adducts, the matrix solution was heated to 50° C. for 10–15 minutes in the presence of cation-exchange resin in ammonium form (200–400 mesh). Samples were prepared for MALDI-TOFMS analysis by mixing 1 µl dialyzed aqueous solution of the following two compounds, $^{3'}$TTCGAATTTGGTAC (SEQUENCE ID No. 1) and $^{5'}$p~CTTAAAC~p (SEQUENCE ID No. 3 in Table 2) (50 pmol/µl). Octadecathymidilate (also known as $p(T)_{18}$) was added as an internal calibrant, whose doubly deprotonated molecular ions were used to calibrate the mass spectra. 0.5 µl of the mixture solution was deposited on a stainless steel target, followed by the deposition of some cation-exchange resin beads in ammonium form (200–400 mesh). The amount of the resin beads was such that the beads covered approximately one half of the sample area. The solution was air dried. Negative ion mass spectra were acquired with a Bruker Reflex MALDI-TOF mass spectrometer in the linear mode. All spectra were summed results of 10 laser shots.

2. Oligonucleotide synthesis

The oligonucleotides used were complementary to a segment of gag region of HIV, described in Temsamani et al., supra. Oligonucleotides were synthesized on an automated synthesizer (MilliGen/Biosearch 8700) with an 18-atom linker on the 3'-end or 5'-end. Two phosphoroamidite synthones were used to introduce the phosphorylated spacer group at the end of the oligonucleotide. Spacer phosphoroamidite (Clontech), (X), with an 18-atom linker, and 5'-phosphate ON (Cruachem), (Y), were used according to the manufacturers' protocols. To prepare 5'-derivatives (after synthesis of the desired sequence), oligonucleotides were coupled successively with X and Y on polymer support. For the 3'-derivatives, polymer support with any attached nucleoside (N) was treated successively with Y and X, and then the synthesis of oligonucleotide continued as desired. After full deprotection, oligonucleotides were purified by ion-exchange HPLC on a PartiSphere SAX cartridge (Whatman) and finally desalted on Sep-Pak $C_{18}$ cartridges (Waters).

3. Synthesis of Netropsin and Distamycin derivatives of oligonucleotides

The procedure is based on a method previously described for oligonucleotides (Zarytova et al., *Biophosphates and the Analogues, Syntheseis Structure, Metabolism and Activity* (Elsevier, Amsterdam), p. 149–164, 1987, which is hereby incorporated by reference) and for phosphorothioate oligonucleotides (Amirkhanov and Zarytova, *Nucleotides v.* 14, p.935–937, 1995, which is hereby incorporated by reference). An oligonucleotide (ODN) with a terminal phosphate group (30–50 O.D.$_{260}$) was precipitated as a cetyltrimethylammonium salt and dried in vacuo. ODN were then dissolved in 60 μl dimethyl sulfoxide (DMSO) and 10 mg of dimethylaminopyridine (DMAP), and 10 mg of 2.2'-dipyridyl disulfide (Py$_2$S$_2$), and 10 mg of triphenylphosphine (Ph$_3$P) were added to the reaction mixture. After 20–30 minutes at room temperature, activated oligonucleotide derivative was precipitated by ether and reprecipitated twice from DMSO by ether to eliminate the excess of activating agents. The mixture of Netropsin (or Distamycin) (1 mg) and DMAP (15 mg) in 120 μl of dimethylformamide (DMF) was added to the activated oligonucleotide in 20 μl of DMF. After 15–20 hours, the products were precipitated by 2% LiClO$_4$ in acetone and separated by subsequent ion-exchange and ion-pair HPLC (FIG. 1). The desired products were desalted on a Waters Sep-Pak C$_{18}$ cartridge by the following procedure. The oligonucleotide derivative was supplied on a cartridge in water, washed successively by water (3 ml) and 5% acetonitrile (3 ml), eluted by 50% acetonitrile (2 ml), and then evaporated. The yield of Netropsin and Distamycin derivatives of oligonucleotides amounted to 60%–70% during the reaction. However, after isolation, the overall yield was 15%–20%.

The Netropsin and Distamycin were attached through a phosphorylated tether to the terminal phosphate of an oligonucleotide as shown below:

using the corresponding ε values at 260 and 320 nm (Zimmer and Wahnert, *Prog. Biophys. Molec. Biol.* V.47. P.31–112, 1986) (ε at 260 nm was assumed as a sum of the ε$_{260}$ values of oligonucleotide and Netropsin or Distamycin). The calculated molar ratios were close to the expected value of 1:1 (or 2:1 in oligonucleotide 5'Distamycin p~CTTAAAC~p Distamycin, SEQUENCE ID No. 3).

To further explore the integrity of the Netropsin compound, MALDI-TOFMS was used. As discussed above, the Netropsin conjugate spiked with an internal standard, showed a negative ion mass spectra acquired in the linear mode. The MALDI-TOFMS results confirmed that the proper netropsin-oligonucleotide conjugates were produced. Furthermore, each of the conjugates were the dominating compounds in the mixture. The molecular weight of 5'-GAAGCT-TAAA~p Netropsin was determined and the result agreed with the expected molecular weight (3896.43).

The Netropsin derivatives of oligonucleotides were exposed to ammonium hydroxide or water and the rate of decomposition was measured by ion-exchange chromatography to determine the stability of the molecules. The compositions were found to be stable in water for at least 1 week at room temperature and for 3–4 months at 4° C. The compositions of (CT)$^5$p-Netropsin and (CT)$^5$p-acetamidine, however, decomposed in concentrated ammonium hydroxide (τ$_{1/2}$=50–150 minutes). The guanidino derivative ((CT)$^5$p-guanidine) was stable under these conditions for at least 2 hours. It was observed that the (CT)$^5$p-guanidine decomposed by a completely different pathway.

Example 2

Antisense Oligonucleotides Conjugated to Netropsin or Distamycin Enhance the Stability of Oligonucleotide/DNA Complexes.

The effects of free Distamycin and Netropsin or Distamycin and Netropsin conjugated to oligonucleotides are shown in Tables 1 and 2 (Distamycin in Table 1 and

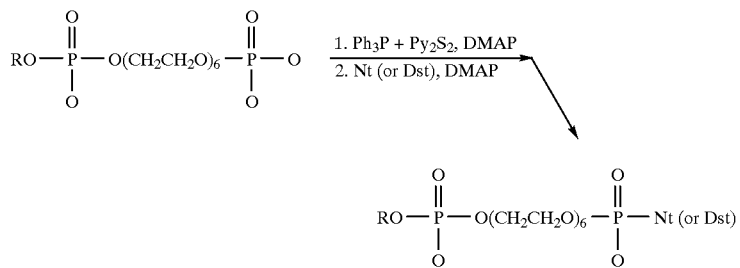

Results:

The netropsin (distamycin)-oligonucleotide conjugates were isolated by successive ion-exchange and ion-pair chromatography as described above. The absorption of Netropsin and Distamycin derivatives was beyond 300 mm in the UV spectra and thus confirmed the presence of N-methylpyrrolecarboxamide groups in the products. The molar ratios of peptide/oligonucleotide were determined Netropsin in Table 2). The addition of just one equivalent of Distamycin to the duplex results in the appearance of two maxima on the differential melting curves (rows 2 and 7 of Table 1). Addition of a second equivalent of Distamycin to the mixture produced a maximum on the differential melting curves (rows 3 and 8 demonstrating the existence of complex with the Distamycin/duplex ratio 2:1).

TABLE 1

INFLUENCE OF THE FREE AND ATTACHED Dst ON THE VALUES OF THE DUPLEXES

| row | duplex | | $T_m$, °C. | $\Delta T_m$, °C. | $\Delta\Delta T_m$, °C. |
|---|---|---|---|---|---|
| 1 | 3'TTCGAATTTGGTAC<br>5'CTTAAACCA | SEQ. ID No. 1<br>SEQ. ID No. 2 | 29.5 | | |
| 2 | 3'TTCGAATTTGGTAC + Dst[a]<br>5'CTTAAACCA | SEQ. ID No. 1<br>SEQ. ID No. 2 | 31.2<br>47.0 | 17.5 | |
| 3 | 3'TTCGAATTTGGTAC + Dst[b]<br>5'CTTAAACCA | SEQ. ID No. 1<br>SEQ. ID No. 2 | 48.1 | 18.6 | |
| 4 | 3'TTCGAATTTGGTAC<br>5'CTTAAACCA~pDst | SEQ. ID No. 1<br>SEQ. ID No. 2 | 29.2 | −0.8 | |
| 5 | 3'TTCGAATTTGGTAC<br>5'Dstp~5'CTTAAACCA | SEQ. ID No. 1<br>SEQ. ID No. 2 | 30.3 | 0.3 | |
| 6 | 3'TTCGAATTTGGTAC<br>5'p~CTTAAAC~p | SEQ. ID No. 1<br>SEQ. ID No. 3 | <15 | | |
| 7 | 3'TTCGAATTTGGTAC + Dst[a]<br>5'p~CTTAAAC~p | SEQ. ID No. 1<br>SEQ. ID No. 3 | ~20<br>30.0 | >15 | |
| 8 | 3'TTCGAATTTGGTAC + Dst[b]<br>5'p~CTTAAAC~p | SEQ. ID No. 1<br>SEQ. ID No. 3 | 33 | >18 | |
| 9 | 3'TTCGAATTTGGTAC<br>5'Dstp~CTTAAAC~pDst | SEQ. ID No. 1<br>SEQ. ID No. 3 | 44.8 | >30 | 11.8 |

[a]One of free Dst per duplex were added
[b]two equivalents of free Dst per duplex were added.
Concentration of oligonucleotides, 3.7 × 10$^{-6}$ M; buffer: 0.17 M NaCl, 0.01 M Na-phosphate, pH 7.3.

One molecule of Distamycin covalently attached to either the 5'-or 3'-terminal phosphate of an oligonucleotide containing a 5' . . . TTAAA . . . sequence had virtually no influence on the stability of the duplex with the complementary oligonucleotide (Table 1, rows 4 and 5). However, the presence of two Distamycin residues (at both ends of oligomer 5'p~CTTAAAC~p) dramatically increased the melting temperature ($\Delta T_m$>30° C.) of the duplex of SEQ. ID Nos. 1 and 3 (Table 1, row 9). Two attached Distamycin residues had a stronger impact on the $T_m$ value than did two free molecules of Distamycin per duplex (Table 1, row 9 versus row 8).

TABLE 2

INFLUENCE OF THE FREE AND ATTACHED Nt ON THE TM VALUES OF THE DUPLEXES

| row | duplex | | $T_m$, °C. | $\Delta T_m$, °C. | $\Delta\Delta T_m$, °C. |
|---|---|---|---|---|---|
| 1 | 3'ATGCCTTCGAATTTGGTA<br>5'p~CTTAAACCA | SEQ. ID No. 4<br>SEQ. ID No. 2 | 25.5 | | |
| 2 | 3'ATGCCTTCGAATTTGGTA + Nt<br>5'p~CTTAAACCA | SEQ. ID No. 4<br>SEQ. ID No. 2 | 40 | 14.5 | |
| 3 | 3'ATGCCTTCGAATTTGGTA<br>5'Ntp~CTTAAACCA | SEQ. ID No. 4<br>SEQ. ID No. 2 | 50.8 | 25.3 | 10.8 |
| 4 | 3'ATGCCTTCGAATTTGGTA<br>5'AAGCTTAAAC~p | SEQ. ID No. 4<br>SEQ. ID No. 5 | 32.5 | −0.8 | |
| 5 | 3'ATGCCTTCGAATTTGGTA + Nt<br>5'AAGCTTAAAC~p | SEQ. ID No. 4<br>SEQ. ID No. 5 | 44.1 | 11.6 | |
| 6 | 3'ATGCCTTCGAATTTGGTA<br>5'AAGCTTAAAC~pNt | SEQ. ID No. 4<br>SEQ. ID No. 5 | 57.8 | 25.3 | 13.7 |
| 7 | 3'ATGCCTTCGAATTTGGTA<br>5'GAAGCTTAAA~p | SEQ. ID No. 4<br>SEQ. ID No. 6 | 30.2 | | |
| 8 | 3'ATGCCTTCGAATTTGGTA + Nt<br>5'GAAGCTTAAA~p | SEQ. ID No. 4<br>SEQ. ID No. 6 | 38.4 | 8.2 | |
| 9 | 3'ATGCCTTCGAATTTGGTA<br>5'GAAGCTTAAA~pNt | SEQ. ID No. 4<br>SEQ. ID No. 6 | 51.2 | 21 | 12.8 |
| 10 | 3'ATGCCTTCGAATTTGGTA<br>5'AAGCTTAAAC~p (P=S) | SEQ. ID No. 4<br>SEQ. ID No. 5 | 25.5 | | |
| 11 | 3'ATGCCTTCGAATTTGGTA+Nt<br>5'AAGCTTAAAC~p (P=S) | SEQ. ID No. 4<br>SEQ. ID No. 5 | 38.3 | 12.8 | |
| 12 | 3'ATGCCTTCGAATTTGGTA<br>5'AAGCTTAAAC~pNt (P=S) | SEQ. ID No. 4<br>SEQ. ID No. 5 | 47.5 | 22 | 9.2 |
| 13 | 3'ATGCCTTCGAATTTGGTA<br>5'GAAGCTTAAA~p (P=S) | SEQ. ID No. 4<br>SEQ. ID No. 6 | 23.5 | | |
| 14 | 3'ATGCCTTCGAATTTGGTA +Nt<br>5'GAAGCTTAAA~p (P=S) | SEQ. ID No. 4<br>SEQ. ID No. 6 | 32.2 | 8.7 | |
| 15 | 3'ATGCCTTCGAATTTGGTA<br>5'GAAGCTTAAA~p (P=S) | SEQ. ID No. 4<br>SEQ. ID No. 6 | 41.8 | 18.3 | 9.6 |
| 16 | 3'ATGCCTTCGAATTTGGTA<br>5'TACGGAAGCTTAAAC~p | SEQ. ID.No. 4<br>SBQ. ID No. 7 | 54.2 | | |

TABLE 2-continued

INFLUENCE OF THE FREE AND ATTACHED Nt ON THE TM VALUES OF THE DUPLEXES

| row | duplex | | $T_m$, °C. | $\Delta T_m$, °C. | $\Delta\Delta T_m$, °C. |
|---|---|---|---|---|---|
| 17 | 3'ATGCCTTCGAATTTGGTA +Nt | SEQ. ID No. 4 | 58.7 | 4.5 | |
| | 5'TACGGAAGCTTAAAC~p | SEQ. ID No. 7 | | | |
| 18 | 3'ATGCCTTCGAATTTGGTA | SEQ. ID No. 4 | 67.1 | 12.9 | 8.4 |
| | 5'TACGGAAGCTTAAAC~pNt | SEQ. ID No. 7 | | | |
| 19 | 5'GTTAAACCA    (hairpin) | SEQ. ID No. 8 | 54.8 | | |
| | p~CAATTTGTC | SEQ. ID No. 18 | | | |
| 20 | 5'GTTAAACCA    (hairpin) | SEQ. ID No. 8 | 63.0 | 8.2 | |
| | p~CAATTTGTC +Nt | SEQ. ID No. 18 | | | |
| 21 | 5'GTTAAACCA    (hairpin) | SEQ. ID No. 8 | 80.9 | 26.1 | 18.0 |
| | Ntp~CAATTTGTC | SEQ. ID No. 18 | | | |
| 22* | 3'CTGAGTGATATGCC | SEQ. ID No. 9 | 22.2 | | |
| | 5'ACTATAC~p | SEQ. ID No. 10 | | | |
| 23* | 3'CTGAGTGATATGCC +Nt | SEQ. ID No. 9 | 30.0 | 7.8 | |
| | 5'ACTATAC~p | SEQ. ID No. 10 | | | |
| 24* | 3'CTGAGTGATATGCC | SEQ. ID No. 9 | 44.2 | 22.0 | 14.2 |
| | 5'ACTATAC~pNt | SEQ. ID No. 10 | | | |
| 25* | 3'CTGAGTGATATGCC | SEQ. ID No. 9 | 35.4 | | |
| | 5'TCACTATAC~p | SEQ. ID No. 11 | | | |
| 26* | 3'CTGAGTGATATGCC +Nt | SEQ. ID No. 9 | 40.6 | 4.6 | |
| | 5'TCACTATAC~p | SEQ. ID No. 11 | | | |
| 27* | 3'CTGAGTGATATGCC | SEQ. ID No. 9 | 54.3 | 18.9 | 14.3 |
| | 5'TCACTATAC~pNt | SEQ. ID No. 11 | | | |
| 28 | 3'GTACCAAATTCGAA | SEQ. ID No. 12 | 27.3 | | |
| | 5'TGGTTTAAG~p | SEQ. ID No. 13 | | | |
| 29 | 3'GTACCAAATTCGAA +Nt | SEQ. ID No. 12 | 41 | 13.7 | |
| | 5'TGGTTTAAG~p | SEQ. ID No. 13 | | | |
| 30 | 3'GTACCAAATTCGAA | SEQ. ID No. 12 | 53.2 | 25.9 | 13.7 |
| | 5'TGGTTTAAG~pNt | SEQ. ID No. 13 | | | |

The same phenomenon (designated as $\Delta\Delta T_m$) was observed for the attached Netropsin (Table 2). The effect of $\Delta\Delta T_m$ was observed either for the 5'-row or 3'-(rows 6 and 9) tethered Netropsin. The free Netropsin molecule enhances the $T_m$ value of the duplex SEQ. ID Nos. 2 and 4 by approximately 15° C. (Table 2, row 2), whereas for the same duplex containing oligoncleotide with the 5'-attached Netropsin residue the $\Delta T_m$ was 25° C. (Table 2, row 3). When Netropsin was tethered to the 3'-end of the oligonucleotide SEQ. ID No. 5 so that it was at the same distance from the AT region in duplex of SEQ. ID Nos. 4 and 5 as it was in duplex SEQ. ID Nos. 2 and 4, but with an opposite orientation, the influence of the Netropsin residue on the $T_m$ value was similar to the previous case ($\Delta T_m$)=25° C.) (Table 2, row 6). When Netropsin was attached to the terminal phosphate (through a tether) directly fixed to the AT sequence (oligonucleotide of SEQ. ID No. 6), its influence was a little less than $\Delta T_m$=21° C.) (Table 2, row 9) than in the previous case when one C residue was inserted between the AT sequence and the terminal phosphate with an attached Netropsin.

When free Netropsin was added to the duplex SEQ. ID Nos. 2 and 4 containing the 5' tethered Netropsin residue, a change in the differential melting curves was observed, although there were no changes after addition of free Netropsin if the Netropsin residue was linked to the 3'-end of oligonucleotides (duplexes SEQ. ID Nos. 4 and 5 and SEQ. ID Nos. 4 and 6).

Relationships between free and attached Netropsin were shown to be the same for oligonucleotide phosphorothioates (oligonucleotides of SEQ. ID Nos. 5 and 6 wherein P=S), although the $T_m$ and $\Delta T_m$ values were less than for the phosphodiesters (Table 2, rows 10–15).

The effect of Netropsin (either free or attached) depended on the length of ODN in the duplex. Duplexes of SEQ. ID Nos. 4 and 7 containing a 15-mer showed less $\Delta T_m$ values than duplexes of SEQ. ID Nos. 4 and 5 or 4 and 6 containing 9-mer or 10-mer (Table 2). However, in each case, tethered Netropsin was more efficient than free Netropsin.

The $\Delta\Delta T_m$ effect was even greater for a hairpin oligonucleotide. When Netropsin was added to the oligonucleotide of SEQ. ID No. 8, $\Delta T_m$ was 8.2° C. In the case of oligo 12b with tethered Netropsin, $\Delta T_m$ was 26.1° C. ($\Delta\Delta T_m$= 17.9° C.) (Table 2, rows 19–21).

Netropsin influences the $T_m$ values of duplexes containing not only five but also four successive AT base pairs (Table 2, rows 22–27). Again, it can be seen that the $\Delta T_m$ and $\Delta\Delta T_m$ values depend on the length of oligonucleotides (Table 2, rows 23 and 24 vs. Rows 26 and 27, respectively).

In contrast to DNA-DNA duplexes, Netropsin has virtually no influence on the thermal stability of DNA-RNA duplexes (Table 2, rows 28–30 vs. rows 31–33). This is in agreement with the well-known datum that Netropsin is a minor groove binder molecule only for B-DNA (Zimner and Wahnert, 1986, supra).

Example 3

Netropsin Conjugated to an Oligonucleotide Interacts With an A-T Rich Sequence.

To clarify if Netropsin conjugated to an oligonucleotide still keeps the ability to recognize and stabilize the double-stranded AT-rich sequences. the effect of free Netropsin was compared to that of oligonucleotide-Netropsin conjugates on the $T_m$ values of duplex 5·21. Conjugated oligonucleotides were either complementary (SEQ. ID No. 16) or not complementary (SEQ. ID No. 17) to the adjacent double-stranded AT-rich region of duplex of SEQ. ID Nos. 4 and 15. Noncomplementary oligonucleotide with the attached Netropsin residue had no influence on the $T_m$ value of duplex of SEQ. ID Nos. 4 and 15 in contrast to free Netropsin, whereas complementary oligonucleotide of SEQ. ID No. 16 changed the $T_m$ like the free Netropsin molecule (Table 2, rows 34–37). In the complex of SEQ. ID Nos. 4, 15 and 16. the influence of tethered Netropsin was virtually the same as for free Netropsin, although in the case of tethered Netropsin, the melting process was more cooperative. It should be noted that the influence of the attached Netropsin on three-membered complex of SEQ. ID Nos. 4, 15 and 16 was lower than that for the two-membered duplexes described previously, and no $\Delta\Delta T_m$ effect was observed in this case.

In all cases, when Netropsin (free or conjugated) is bound to a duplex, its UV spectrum changed as a result of the heat denaturation of this duplex. Normally, Netropsin has an absorption maximum at 296 nm. When Netropsin bound to a duplex at room temperature, this process was accompanied by an increase in absorption beyond 320 nm. On heat denaturation, the UV spectrum of the Netropsin residue were similar to that of nonbound Netropsin, and the absorption of the conjugate at 260 nm increased due to the hypochromic effect for oligonucleotides. Therefore, when heating of the duplex containing Netropsin was carried out at 320 nm, the melting curve was the mirror reflection of that obtained at 260 nm.

Each of the foregoing patents, patent applications and references is hereby incorporated by reference. While the invention has been described with respect to certain embodiments, it should be appreciated that many modifications and changes may be made by those of ordinary skill in the art without departing from the spirit of the invention. It is intended that such modification, changes and equivalents fall within the scope of the following claims.

What is claimed is:

1. A composition of matter comprising:
an oligonucleotide covalently coupled to a peptide, the peptide comprising a plurality of N-methylpyrrolecarboxamides linked to one another by peptide bonds, each N-methylpyrrolecarboxamide having a pyrrole moiety with a carbon atom at the 1C position adjacent a nitrogen atom of the pyrrole moiety, wherein the antisense oligonucleotide is covalently coupled to said peptide via the carbon atom at the 1C position of a terminal N-methylpyrrolecarboxamide of said peptide.

2. The composition of claim 1, wherein the peptide comprises between two and five N-methylpyrrolecarboxamides.

3. The composition of claim 1, wherein the oligonucleotide comprises at least four consecutive nucleotides selected from the group consisting of A and T.

4. The composition of claim 1, wherein the oligonucleotide comprises consecutive nucleotides selected from the group consisting of TTAAA, TTTAA, AATT, TTAAT, AATTA, TAATA, ATTAT, AAAA, TTTT, ATAT, and TATA.

5. The composition of claim 1, wherein the peptide is netropsin.

6. The composition of claim 1, wherein the oligonucleotide is covalently coupled to two of said peptides, one coupled at a 5' end of said oligonucleotide and another coupled at a 3' end of said oligonucleotide.

7. The composition of claim 6, wherein the peptide is distamycin.

8. The composition of claim 1, wherein the oligonucleotide is an antisense oligonucleotide.

9. A composition of matter comprising an oligonucleotide covalently coupled to netropsin, wherein the oligonucleotide is coupled to netropsin via a terminal amidine functionality of netropsin.

10. The composition of claim 9, wherein the oligonucleotide is coupled to only a single netropsin.

11. The composition of claim 9, wherein the oligonucleotide comprises at least four consecutive nucleotides selected from the group consisting of A and T.

12. The composition of claim 11, wherein the oligonucleotide comprises consecutive nucleotides selected from the group consisting of TTAAA, TTTAA, AATT, TTAAT, AATTA, TAATA, ATTAT, AAAA, TTTT, ATAT, and TATA.

13. The composition of claim 9, wherein the oligonucleotide is an antisense oligonucleotide.

14. The composition of claim 11, wherein the oligonucleotide is an antisense oligonucleotide.

15. The composition of claim 12, wherein the oligonucleotide is an antisense oligonucleotide.

16. A composition of matter comprising an oligonucleotide covalently coupled to netropsin, consisting essentially of

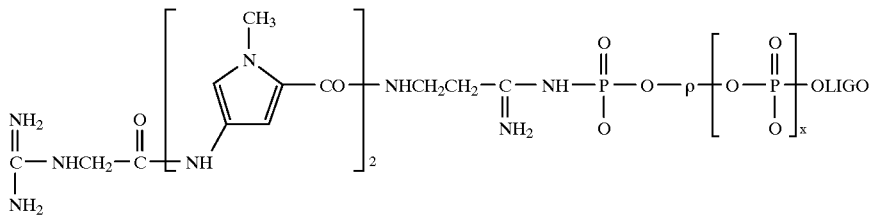

wherein ρ is an organic linker comprising a chain length between 1 and 30 atoms when x=1 or is a bond when x=0.

17. A composition of matter comprising an oligonucleotide having a 5' end and a 3' end, said oligonucleotide covalently coupled to two distamycin's, one distamycin covalently coupled to the 5' end and the other distamycin covalently coupled to the 3' end of said antisense oligonucleotide.

18. The composition of claim 17, wherein the oligonucleotide is coupled to each distamycin via a terminal amidine functionality of each distamycin.

20. The composition of claim 17, wherein the oligonucleotide comprises at least 4 consecutive nucleotides selected from the group consisting of A and T.

21. The composition of claim 19, wherein the oligonucleotide comprises consecutive nucleotides selected from the group consisting of TTAAA, TTTAA, AATT, TTAAT, AATTA, TAATA, ATTAT, AAAA, TTTT, ATAT, and TATA.

22. The composition of claim 17, wherein the oligonucleotide is an antisense oligonucleotide.

23. The composition of claim 20, wherein the oligonucleotide is an antisense oligonucleotide.

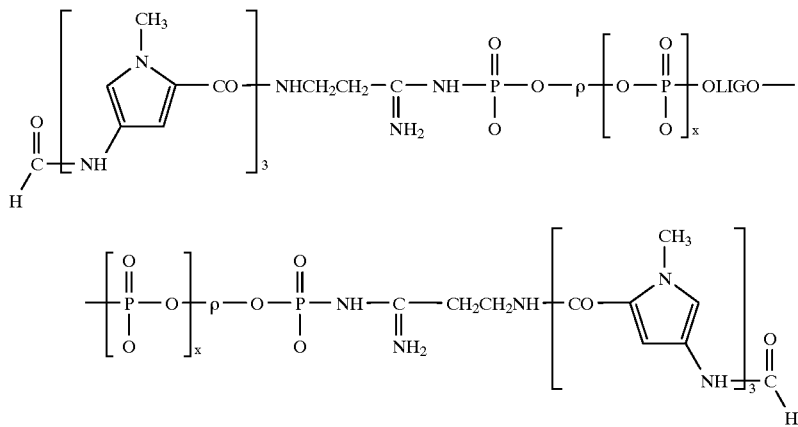

wherein ρ is an organic linker comprising a chain length between 1 and 30 atoms when x=1 or is a bond when x=0.

24. The composition of claim 21, wherein the oligonucleotide is an antisense oligonucleotide.

* * * * *

SEQUENCE LISTING (1) GENERAL INFORMATION:

(iii) NUMBER OF SEQUENCES: 18

(2) INFORMATION FOR SEQ ID NO:1:

(i) SEQUENCE CHARACTERISTICS:
       (A) LENGTH: 14 base pairs
       (B) TYPE: nucleic acid
       (C) STRANDEDNESS: single
       (D) TOPOLOGY: linear (ii) MOLECULE TYPE: Oligodeoxyribonucleotide (iii) HYPOTHETICAL: YES (iv) ANTI-SENSE: NO (xi) SEQUENCE DESCRIPTION: SEQ ID NO:1:

CATGGTTTAA GCTT                                            14

(2) INFORMATION FOR SEQ ID NO:2:

(i) SEQUENCE CHARACTERISTICS:
       (A) LENGTH: 9 base pairs
       (B) TYPE: nucleic acid
       (C) STRANDEDNESS: single
       (D) TOPOLOGY: linear (ii) MOLECULE TYPE: Oligodeoxyribonucleotide (iii) HYPOTHETICAL: YES (iv) ANTI-SENSE: NO (xi) SEQUENCE DESCRIPTION: SEQ ID NO:2:

CTTAAACCA                                                   9

(2) INFORMATION FOR SEQ ID NO:3:

(i) SEQUENCE CHARACTERISTICS:
       (A) LENGTH: 7 base pairs
       (B) TYPE: nucleic acid
       (C) STRANDEDNESS: single
       (D) TOPOLOGY: linear (ii) MOLECULE TYPE: Oligodeoxyribonucleotide (iii) HYPOTHETICAL: YES (iv) ANTI-SENSE: NO (xi) SEQUENCE DESCRIPTION: SEQ ID NO:3:

CTTAAAC                                                     7

(2) INFORMATION FOR SEQ ID NO:4:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: Oligodeoxyribonucleotide (iii) HYPOTHETICAL: YES (iv) ANTI-SENSE: NO (xi) SEQUENCE DESCRIPTION: SEQ ID NO:4:

ATGGTTTAAG CTTCCGTA                                                 18

(2) INFORMATION FOR SEQ ID NO:5:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: Oligodeoxyribonucleotide (iii) HYPOTHETICAL: YES (iv) ANTI-SENSE: NO (xi) SEQUENCE DESCRIPTION: SEQ ID NO:5:

AAGCTTAAAC                                                             10

(2) INFORMATION FOR SEQ ID NO:6:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: Oligodeoxyribonucleotide (iii) HYPOTHETICAL: YES (iv) ANTI-SENSE: NO (xi) SEQUENCE DESCRIPTION: SEQ ID NO:6:

GAAGCTTAAA                                                             10

(2) INFORMATION FOR SEQ ID NO:7:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: Oligodeoxyribonucleotide (iii) HYPOTHETICAL: YES (iv) ANTI-SENSE: NO (xi) SEQUENCE DESCRIPTION: SEQ ID NO:7:

TACGGAAGCT TAAAC                                                     15

(2) INFORMATION FOR SEQ ID NO:8:

(i) SEQUENCE CHARACTERISTICS:

(A) LENGTH: 9 base pairs
            (B) TYPE: nucleic acid
            (C) STRANDEDNESS: single
            (D) TOPOLOGY: linear (ii) MOLECULE TYPE: Oligodeoxyribonucleotide (iii) HYPOTHETICAL: YES (iv) ANTI-SENSE: NO (xi) SEQUENCE DESCRIPTION: SEQ ID NO:8:

GTTAAACCA                                                                          9

(2) INFORMATION FOR SEQ ID NO:9:

(i) SEQUENCE CHARACTERISTICS:
            (A) LENGTH: 14 base pairs
            (B) TYPE: nucleic acid
            (C) STRANDEDNESS: single
            (D) TOPOLOGY: linear (ii) MOLECULE TYPE: Oligodeoxyribonucleotide (iii) HYPOTHETICAL: YES (iv) ANTI-SENSE: NO (xi) SEQUENCE DESCRIPTION: SEQ ID NO:9:

CCGTATAGTG AGTC                                                                    14

(2) INFORMATION FOR SEQ ID NO:10:

(i) SEQUENCE CHARACTERISTICS:
            (A) LENGTH: 7 base pairs
            (B) TYPE: nucleic acid
            (C) STRANDEDNESS: single
            (D) TOPOLOGY: linear (ii) MOLECULE TYPE: Oligodeoxyribonucleotide (iii) HYPOTHETICAL: YES (iv) ANTI-SENSE: NO (xi) SEQUENCE DESCRIPTION: SEQ ID NO:10:

ACTATAC                                                                            7

(2) INFORMATION FOR SEQ ID NO:11:

(i) SEQUENCE CHARACTERISTICS:
            (A) LENGTH: 9 base pairs
            (B) TYPE: nucleic acid
            (C) STRANDEDNESS: single
            (D) TOPOLOGY: linear (ii) MOLECULE TYPE: Oligodeoxyribonucleotide (iii) HYPOTHETICAL: YES (iv) ANTI-SENSE: NO (xi) SEQUENCE DESCRIPTION: SEQ ID NO:11:

TCACTATAC                                                                          9

(2) INFORMATION FOR SEQ ID NO:12:

(i) SEQUENCE CHARACTERISTICS:
            (A) LENGTH: 14 base pairs
            (B) TYPE: nucleic acid
            (C) STRANDEDNESS: single
            (D) TOPOLOGY: linear (ii) MOLECULE TYPE: Oligodeoxyribonucleotide (iii) HYPOTHETICAL: YES (iv) ANTI-SENSE: NO (xi) SEQUENCE DESCRIPTION: SEQ ID NO:12:

AAGCTTAAAC CATG                                                        14

(2) INFORMATION FOR SEQ ID NO:13:

(i) SEQUENCE CHARACTERISTICS:
                  (A) LENGTH: 9 base pairs
                  (B) TYPE: nucleic acid
                  (C) STRANDEDNESS: single
                  (D) TOPOLOGY: linear (ii) MOLECULE TYPE: Oligodeoxyribonucleotide (iii) HYPOTHETICAL: YES (iv) ANTI-SENSE: NO (xi) SEQUENCE DESCRIPTION: SEQ ID NO:13:

TGGTTTAAG                                                               9

(2) INFORMATION FOR SEQ ID NO:14:

(i) SEQUENCE CHARACTERISTICS:
                  (A) LENGTH: 14 base pairs
                  (B) TYPE: nucleic acid
                  (C) STRANDEDNESS: single
                  (D) TOPOLOGY: linear (ii) MOLECULE TYPE: oligoribonucleotide (iii) HYPOTHETICAL: YES (iv) ANTI-SENSE: NO (xi) SEQUENCE DESCRIPTION: SEQ ID NO:14:

AAGCUUAAAC CAUG                                                        14

(2) INFORMATION FOR SEQ ID NO:15:

(i) SEQUENCE CHARACTERISTICS:
                  (A) LENGTH: 9 base pairs
                  (B) TYPE: nucleic acid
                  (C) STRANDEDNESS: single
                  (D) TOPOLOGY: linear (ii) MOLECULE TYPE: Oligodeoxyribonucleotide (iii) HYPOTHETICAL: YES (iv) ANTI-SENSE: NO (xi) SEQUENCE DESCRIPTION: SEQ ID NO:15:

CTTAAACCA                                                               9

(2) INFORMATION FOR SEQ ID NO:16:

(i) SEQUENCE CHARACTERISTICS:
                  (A) LENGTH: 7 base pairs
                  (B) TYPE: nucleic acid
                  (C) STRANDEDNESS: single
                  (D) TOPOLOGY: linear (ii) MOLECULE TYPE: Oligodeoxyribonucleotide (iii) HYPOTHETICAL: YES

```
        (iv) ANTI-SENSE: NO (xi) SEQUENCE DESCRIPTION: SEQ ID NO:16:

ACGGAAG                                                                     7

(2) INFORMATION FOR SEQ ID NO:17:

(i) SEQUENCE CHARACTERISTICS:
             (A) LENGTH: 7 base pairs
             (B) TYPE: nucleic acid
             (C) STRANDEDNESS: single
             (D) TOPOLOGY: linear (ii) MOLECULE TYPE: Oligodeoxyribonucleotide (iii) HYPOTHETICAL: YES (iv) ANTI-SENSE: NO (xi) SEQUENCE DESCRIPTION: SEQ ID NO:17:

TCTCTCT                                                                     7

(2) INFORMATION FOR SEQ ID NO:18:

(i) SEQUENCE CHARACTERISTICS:
             (A) LENGTH: 9 base pairs
             (B) TYPE: nucleic acid
             (C) STRANDEDNESS: single
             (D) TOPOLOGY: linear (ii) MOLECULE TYPE: Oligodeoxyribonucleotide (iii) HYPOTHETICAL: YES (iv) ANTI-SENSE: NO (xi) SEQUENCE DESCRIPTION: SEQ ID NO:18:

CTGTTTAAC                                                                   9
```